(12) United States Patent
Bhosale et al.

(10) Patent No.: US 7,335,495 B2
(45) Date of Patent: Feb. 26, 2008

(54) **PROCESS FOR THE ISOLATION OF PHARMACEUTICAL COMPOUND CYCLOSPORIN A FROM FUNGUS *FUSARIUM NIVALE***

(75) Inventors: Siddarth Bhosale, Goa (IN); Chandrakant Govid Naik, Goa (IN); Perunnikulath Subrayan Parameswaran, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/106,828

(22) Filed: Mar. 27, 2002

(65) Prior Publication Data

US 2003/0186856 A1    Oct. 2, 2003

(51) Int. Cl.
*C12P 21/04* (2006.01)

(52) U.S. Cl. .................... 435/71.1; 435/71.3; 435/243; 530/317

(58) Field of Classification Search ............... 435/71, 435/71.1; 530/317
See application file for complete search history.

(56) References Cited

OTHER PUBLICATIONS

Sawai K , et al.. Isolation and properties of two antifungal substances from *Fusarium solani*. Agric. Biol. Chem. 45: 1223-1228, 1981.*

* cited by examiner

*Primary Examiner*—Irene Marx
(74) *Attorney, Agent, or Firm*—Dinesh Agarwal, P.C.

(57) ABSTRACT

The present invention describes the development and standardization of a facile method for the isolation and purification of cyclosporin A from a new source, viz., *Fusarium nivale* and evaluation of its novel antifungal activity against the food spoilage *Aspargellius* strains and few dermatophytes.

3 Claims, 7 Drawing Sheets

Cyclosporin A

FIGURE 7

PROCESS FOR THE ISOLATION OF PHARMACEUTICAL COMPOUND CYCLOSPORIN A FROM FUNGUS FUSARIUM NIVALE

FIELD OF THE INVENTION

The present investigation relates to a simplified method for the isolation of pharmaceutically important cyclosporin-A from a new fungal source, *Fusarium nivale* (Fres,) Ces., and evaluation of its in vitro activity against food spoilage *Aspergillus* strains and few dermatophyles. The fungus was isolated from the leaves of an associated mangrove plant *Portersia coarctata* (Roxb.)

BACKGROUND AND PRIOR ART REFERENCES

The fungus *Fusarium solani* is a well-known source for many bioactive molecules including terpenoids, aromatic compounds, peptides and proteins (Mall, O. P. and S. K. Chauhan, International Bioscience Series 15, 1990), Haymecins A-C toxic to microalgae (Chen et al., Halymecins, 44:10, 1996). Trichothecenes and Zearalenone the well known mycotoxins (Ureno, et al., 3: 1977), gibberellins, the plant growth hormones (Dilip et al., Hand book of Applied mycology: Fungal Biotechnology, 4: (1992), cyclosporin A and C having strong antifungal activity against plant pathogenic fungi (Smawi, et al., Agric. Biol. Chem. 45: 5, 1981) are a few such examples.

Cyclosporins are cyclic oligopeptides exclusively produced by fungi belonging to the genus *Tolypocladium, Cylindrocarpon* and *Fusarium* spp. They were first reported from; *Cylondrocarpon lucidum* (Booth) and *Tolypocladium inflatum* (grams), two fungi from USA and Norway, respectively. Apart from being strong fungicides, these compounds also exhibnit antiparasdtitic (J. Weiser and V. Matha. J. Inver. Pathol. 51, 1988) anti-inflammatory (C. R. Stiller and G. Opelz. Transplant Proc. 23, 1991) and immunosuppressive (Z. Rahacek and Z. DeXiu. Process Biochem. 26, 1991) properties. In all, nine cyclosporin analogues viz, cyclosporine A-I are presently known. Among these, the immunosuppressive activity of cyclosporin A is very promising and is widely being used clinically after kidney and other organ transplant surgeries. Cyclosporin A is presently produced by mass culture of fungal strains. Two major problems faced by mycologists and chemists in this endeavor are:
1. Optimizing the yield and improving the selectivity in the production of cyclosporin A.
2. Simplifying the purification procedure.

Industrial production of cyclosporin A involves submerged culture of the fungus, extraction from the fungal mass using methanol/acetone and purification of the extracts using partition/ion exchange chromatography.

OBJECT OF THE INVENTION

The main object of the present invention is to isolate cyclosporin A, a cyclic peptide of biomedical interest from a new fungal source *Fusarium nivale*.

Another object of the invention is to modify the culture media to maximize the yield of cyclosporin A and minimize the production of other cyclosporins.

Still another object of the invention is to develop a simple and facile method for the extraction, isolation and purification of cyclosporin A from the culture mat.

Yet another object of the invention is to describe the in vitro antifungal activity of cyclosporin A against food spoilage of *Aspergillus* strains and some of the commonly occurring dermatophytes.

SUMMARY OF THE INVENTION

Accordingly, the present invention describes the development and standardization of a facile method for the isolation and purification of cyclosporin A from a new source, viz., *Fusarium nivale* and evaluation of its novel antifungal activity against the food spoilage *Aspargellius* strains and few dermatophytes.

BRIEF DESCRIPTION OF ACCOMPANYING DRAWINGS

In the drawing accompanying this specification

DETAILED DESCRIPTION OF THE INVENTION

Figure 1:
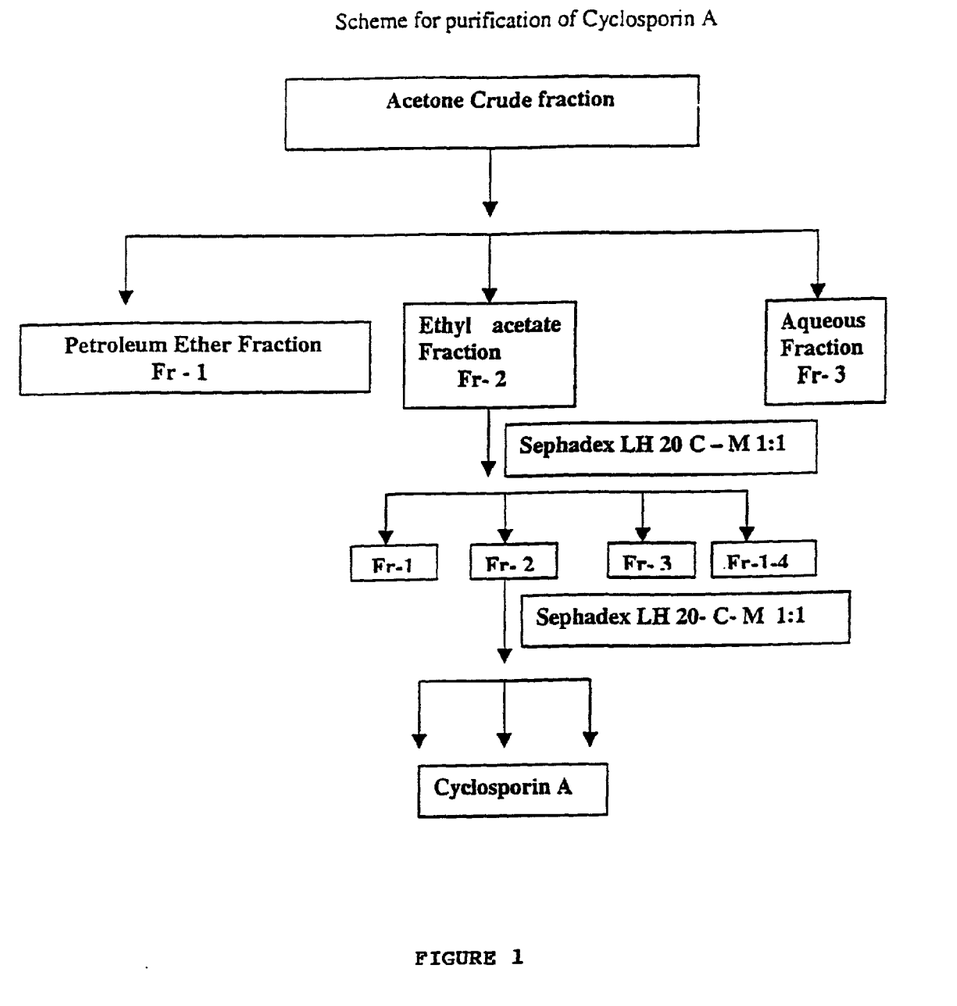
FIG. 1 represents the scheme used for the purification of the compound, cyclosporin A, from the crude acetone extract of *Fusarium nivale* mycelial cells.
Figure 2:
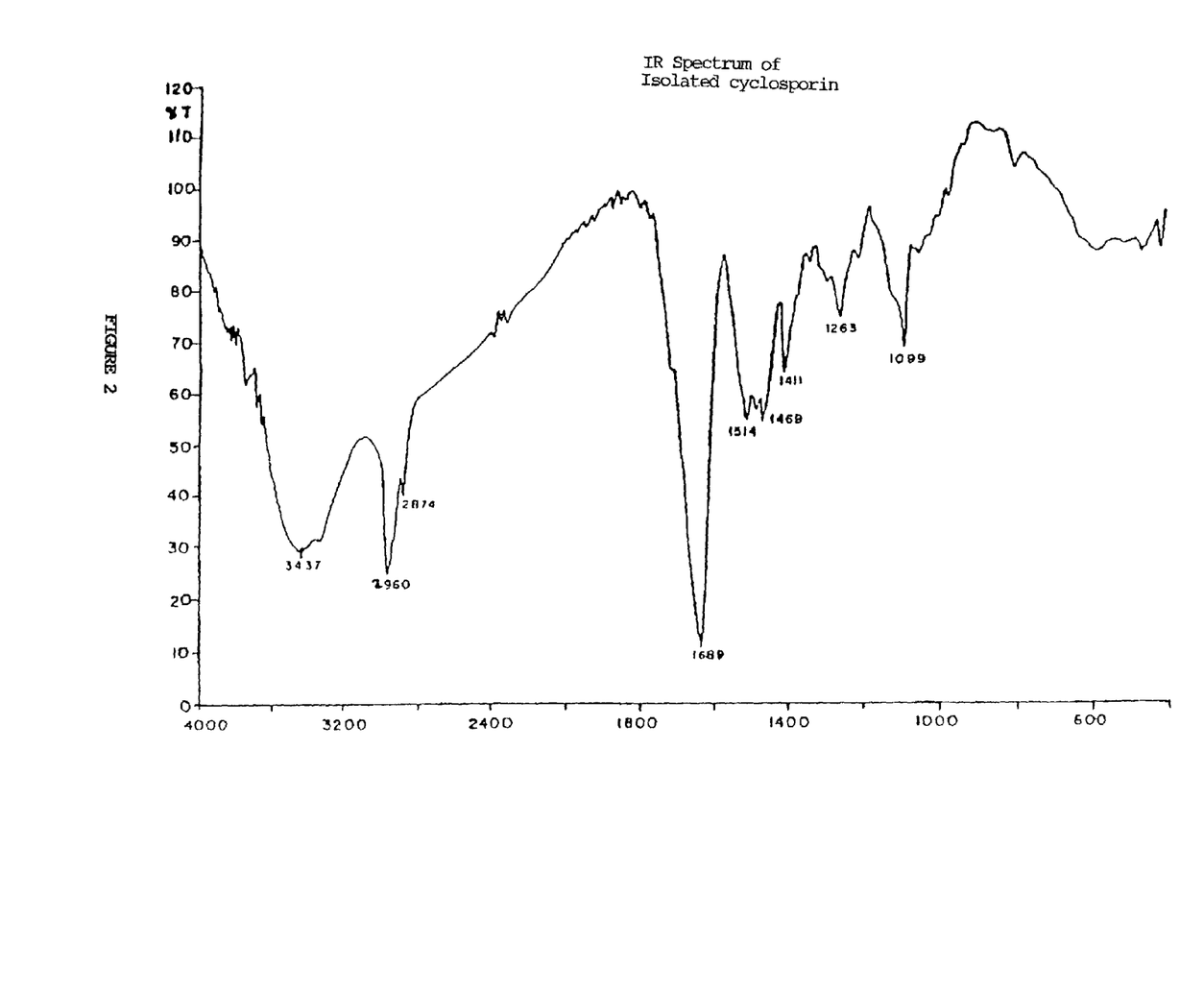
FIG. 2 represents the infra red spectrum of cyclosporin A.
Figure 3:
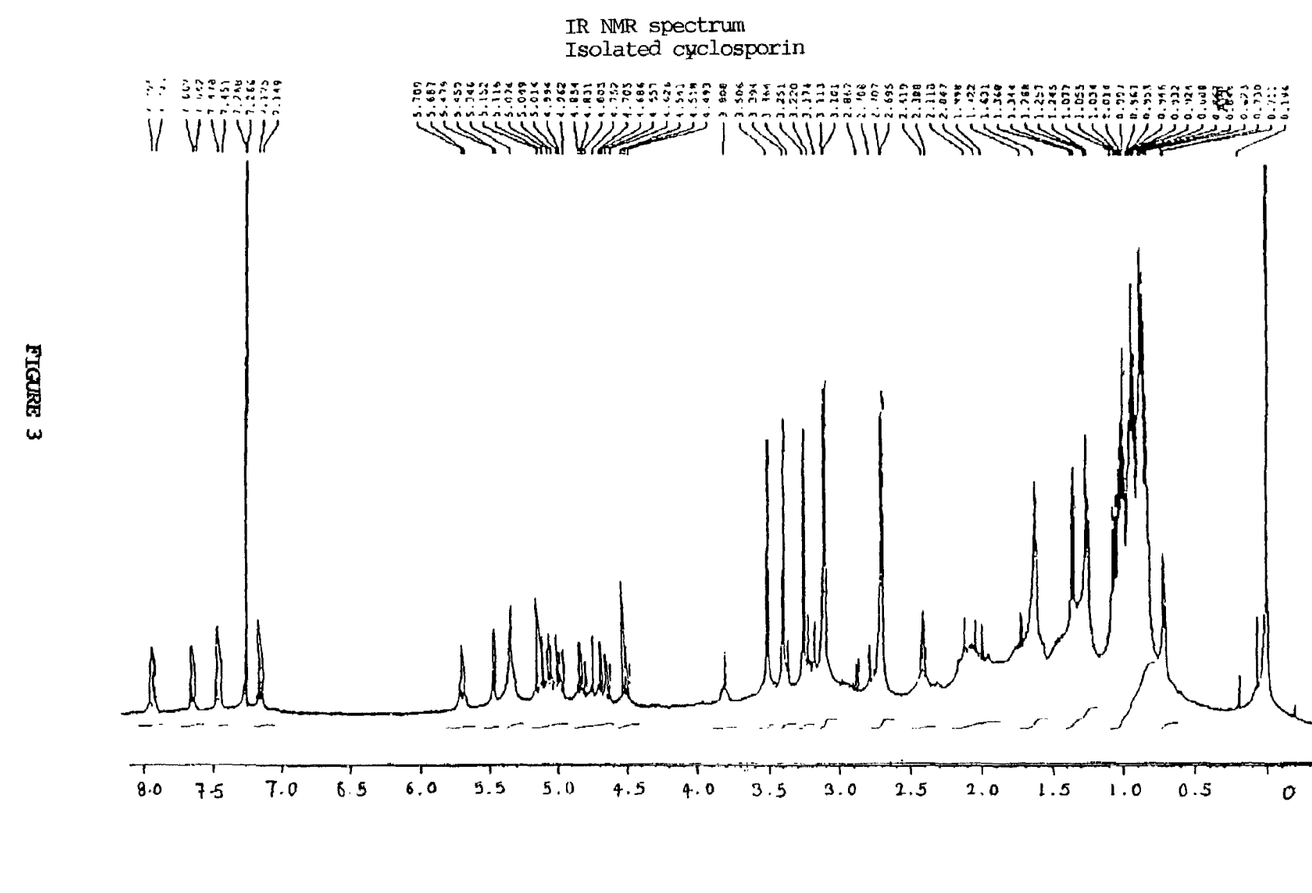
FIG. 3 represents the $^1$H NMR spectrum of the compound.
Figure 4:
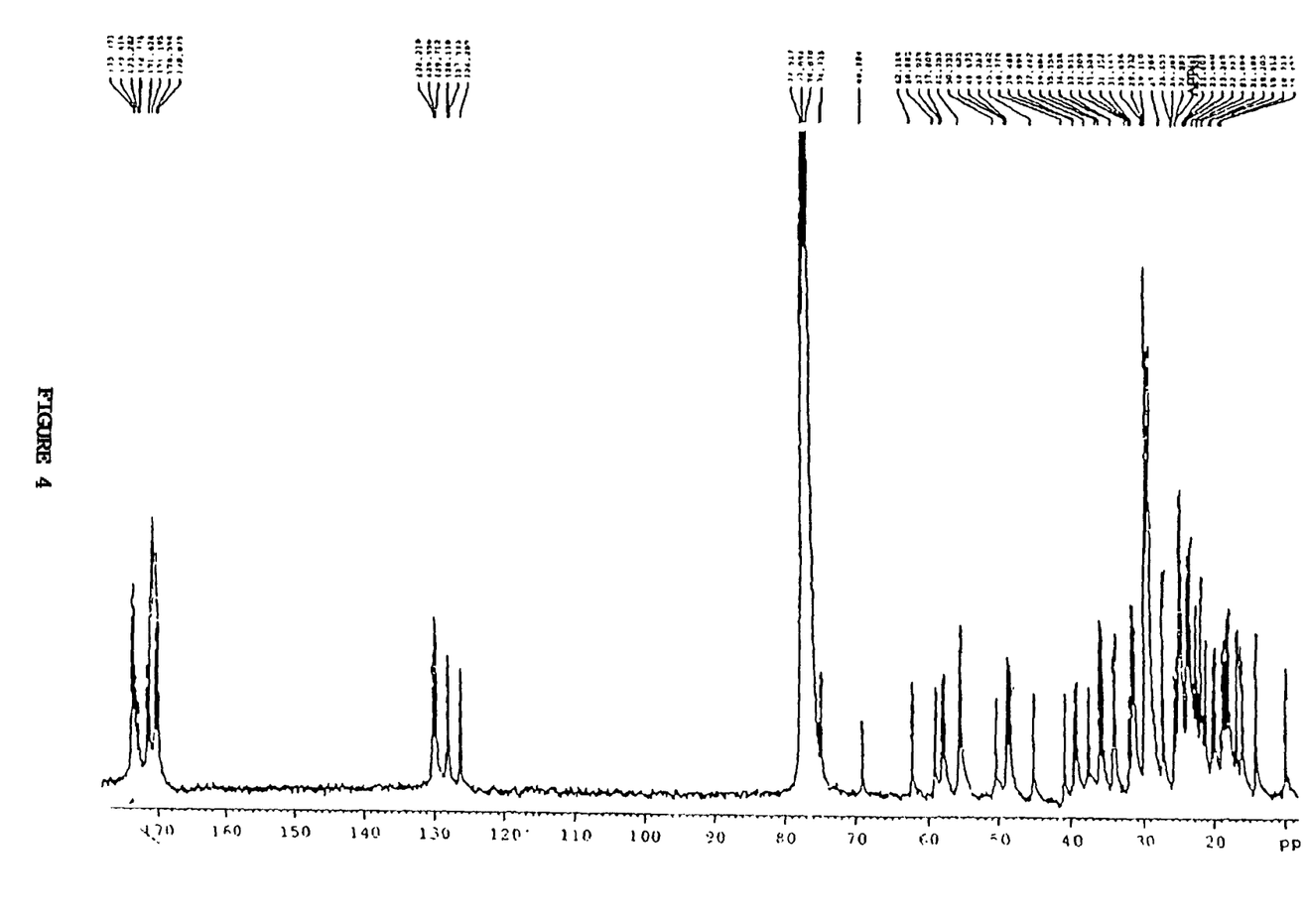
FIG. 4 represents the $^{13}$C NMR spectrum of the compound.
Figure 5:
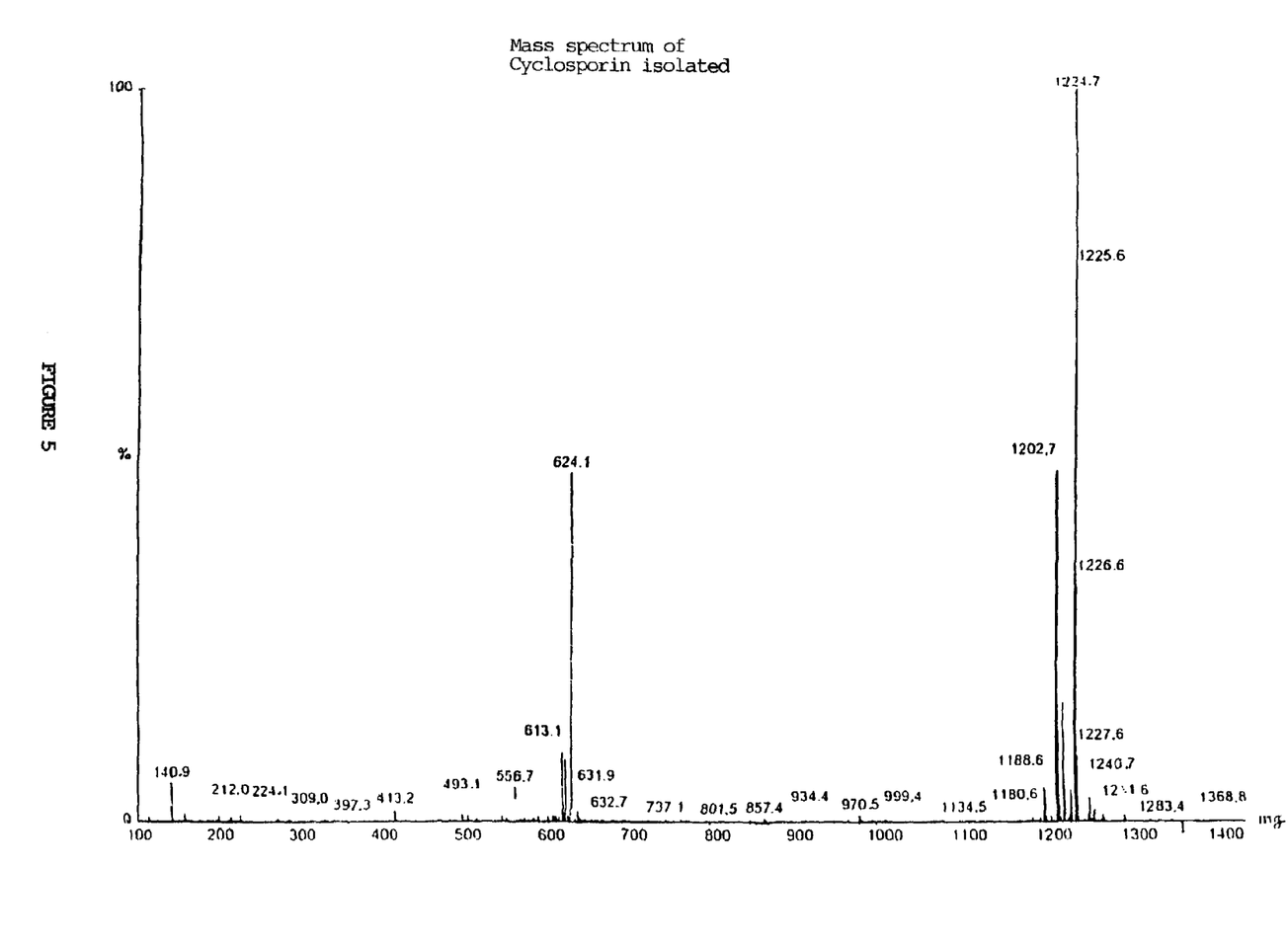
FIG. 5 represents the mass spectrum of the compound.
Figure 6:
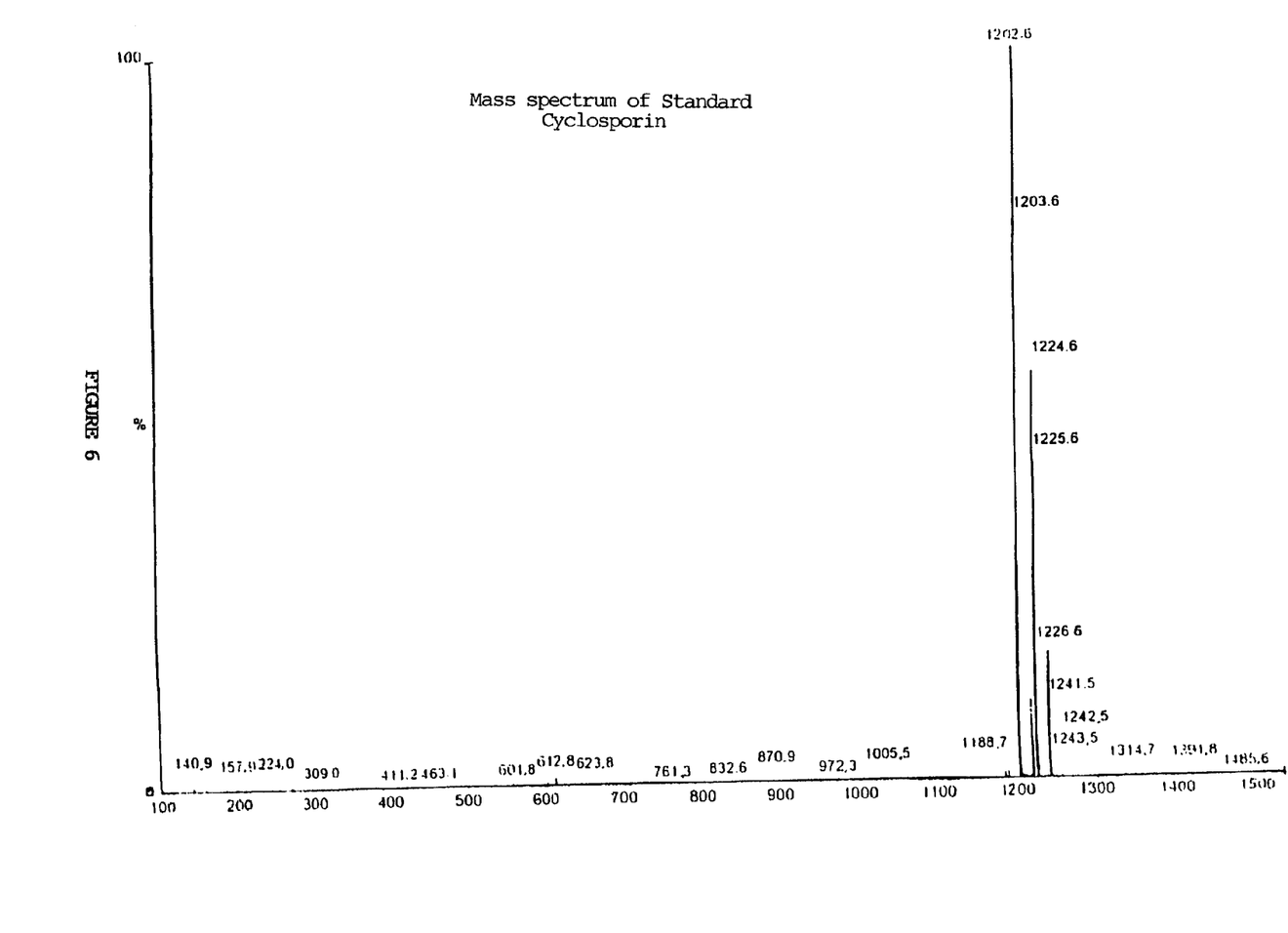
FIG. 6 represents mass spectrum of the standard cyclosporin A.
Figure 7:
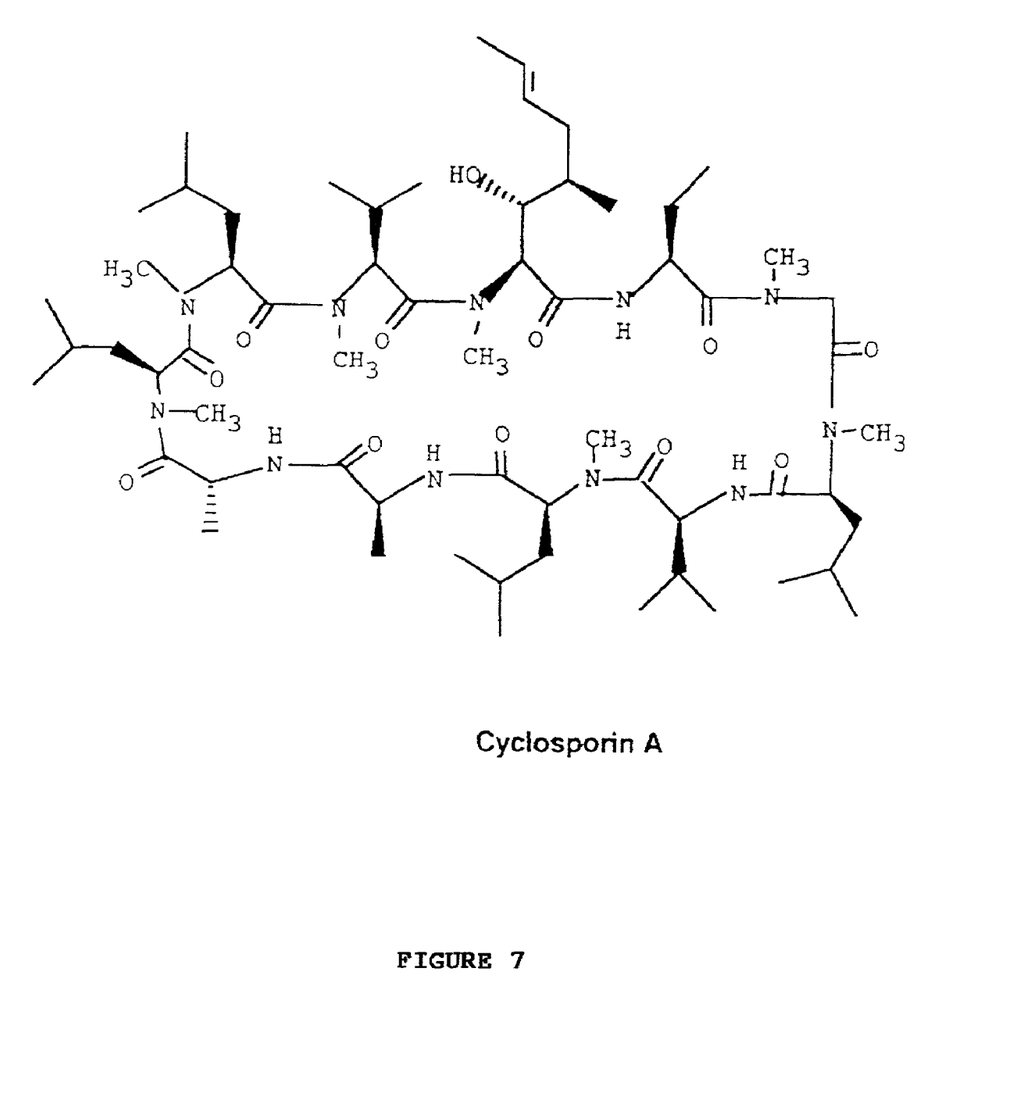
FIG. 7 represents the structure of the purified compound.

The present invention relates to the development and standardization of a facile method for the isolation and purification of cyclosporin A from a new fungal source *Fusarium nivale*. The invention provides optimum culture conditions and suitable media for the production of cyclosporin A, almost exclusively. The isolation and purification procedure of cyclosporin A from the crude acetone extract of the fungal mat has also been greatly simplified. It further explains wide range of in vitro antifungal activity and MIC of cyclosporin A against food spoilage *Aspergillus* strains and a few dermatophytes. Accordingly, the present invention provides a process for the isolation of pharmaceutically active compound cyclosporin A from the fungus *Fusarium nivale*, the process comprising the steps of:
a) washing the leaves of *Porteresia coarctata* with sterile sea water,
b) growing the fungus on washed leaves of *Porteresia coarctata* of step (a),
c) identifying the grown fungus of step (b) as *Fusarium nivale*,
d) purifying the colony of fungus *Fusarium* of step (c),
e) transferring the purified colony of step (d) with the help of nichrome loop into sterile culture media,
f) growing the culture media of step (e) containing nutrient both with sea water and standard medium for three weeks under stationary condition.
g) removing biomass of the fungi of step (d) at optimum growth condition and energy,
h) freeze drying the biomass of step (g),
i) extracting the freeze dried bio mass of step (h) with a ketonic solvent, j) concentrating the ketonic solvent extract of step (i) under reduced pressure around temperature of 30° C. to obtain an extract, k) adding water to the extract of step (j), l) extracting the aqueous extract of step (k) with petroleum ether, followed by ethyl acetate, separating the organic layers and aqueous solution, m) evaporating the ethylacetate extract of step (l) to obtain concentrated ethyl acetate extract, and n) purifying concentrated ethyl acetate extract of step (in) by repeated gel chromatography using Sephadex LH-20, eluting with chloroform-methanol (1:1) to obtain pure cyclosporin A.

In an embodiment of the invention, the sterile culture media used in step (c) is Czapek Malt Agar.

One more embodiment of the invention, the ketonic solvent used in step (g) is selected from a group consisting of acetone, ethyl methyl ketone or methyl isobatyl ketone and preferably acetone.

Still another embodiment of the invention relates to a process wherein, the said compound cyclosporin A is found to be active in vitro against food spoilage *Apergillus* stains selected from *A. fresenii, A. niger, A japonicus,* commonly occurring thermatophytes selected from *Trichophyone mentagophytes, T. tinsurinus, T. violoceium, Candica* specis and *cryptococus neoformans.*

Still another embodiment, the said compound cyclosporin A is isolated for the first time from fungus belonging to genus *Fusarium*.

The present invention provides an improved process for the isolation of cyclosporin A, said process comprising the steps of:

Modifying culture conditions and culture media for maximizing the yield of cyclosporin A and minimizing the production of other cyclosporins.

Preparing the crude acetone extract of the fungal mat.

Subjecting the crude acetone extract to solvent-solvent partitioning to prepare cyclosporin A enriched organic fraction.

Subjecting the organic fraction thus obtained to gel permeation chromatography (GPC) over Sephadex LH-20 using chloroform:methanol (in various proportion) as eluant to yield pure cyclosporin A.

In an embodiment the process of culturing the fungus *F. nivale* isolated from and associated mangrove leaf of *Porteresia coarctata* was carried out in Czapek Malt Agar (CMA). Mass culture was carried out in the Nutrient broth (Hi-media, India Ltd.) in order to maximize the yield of cyclosporin A.

In another embodiment the cyclosporin A rich fraction was extracted from the fungal mat using methanol/acetone as solvent.

In yet another embodiment the relatively non polar cyclosporin A was extracted using a lipophillic solvent such as ethyl acetate, chloroform etc in to the organic layer.

In still another embodiment, the above organic fraction was purified over Sephadex LH-20 to yield a white solid. The structure of the compound thus isolated was established to be cyclosporin A after comparison of its IR, NMR (Raman et al., Process Biochem 34, 1999) and MS data with spectra of standard cyclosporin A.

The invention is further explained with the help of the following examples and should not be construed as to limit the scope of the invention.

EXAMPLE I

Associated mangrove plant *Porteresia coarctata* (Roxb.) was collected from Chorao Island along the Mandovi estury of Goa, India. *Porteresia coarctata* is a plant belonging to *Monocotyledonae* plant belonging to the family, Granimae. After collection, plant leaves were rinsed with sterile seawater to remove adherent particles and detritus material. Leaves were kept in moist chamber for two weeks to allow the fungus to grow and sporulate. After three weeks of sporulation fungal material was removed and surface sterilized using 0.5% sodium hypochlorite for three minutes, and washed with small brush in sterile distilled water. Identification of the fungal material was done using standard keys.

EXAMPLE II

Fungus was identified as *Fusarium nivale* (Fres.)Ces. The purified *Fusarium* colony was transferred with the help of nichrome loop into sterile culture media (Czapek Malt Agar). This culture was grown in a 2 liter flask in the culture media (Nutrient broth) with 50% sea water as a standard medium for three weeks under stationary condition. Fungi at the optimum growth condition and energy biomass were removed and freeze dried.

EXAMPLE III

Nutrient broth (Hi-Media India Ltd) was used for mass culture. The mycelium cells (7.8935 g dry wt.), were extracted with Acetone. The process of extraction was repeated thrice. The acetone extract was filtered and the filtrate was concentrated under reduced pressure at 30° C. to yield acetone extract.

EXAMPLE IV

The acetone extract was fractionated into petroleum ether, ethyl acetane and aqueous fractions. The ethyl acetate fraction was repeatedly chromatographed over Sephadex LH20 with $CHCl_3$-methanol (1:1). Fractions of 5 ml each were collected in separate test tubes. Compound eluting in test tube no. 2-4 (15 ml) were pooled together (68 mg), identified as cyclosporin A after comparison of its IR, NMR (Ramana etal., Process Biochem. 34, 1999) and MS data with that of authentic sample.

EXAMPLE V

Mycological broth (Hi-Media India Ltd.) was used for mass culture. The mycelium cells (7.7266 g dry wt.) were extracted with methanol. The process of extraction was repeated thrice. The methanol extract was filtered and the filtrate concentrated under reduced pressure at 30° C. to yield crude extract.

EXAMPLE VI

The methanol extract was fractionated into petroleum ether, ethyl aceatate, $ChCl_3$, aqueous fractions. The chloroform fraction was chromatographed repeatedly over Sephadex LH-20 with $CHCl_3$-methanol (1:1). Fraction of ~5 ml each were collected in separate test tubes. Compound eluting in test tube no. 5-6 (~10 ml) were pooled together (~3 mg), identified as cyclosporin A after comparison of its IR, NMR (Ramana et al., Process Biochem 34, 1999) and MS data with that of authentic samples.

Antifungal Activity of the Composition of the Invention

The following assay method was utilized to demonstrate in vitro antifungal effectiveness of composition of the invention as reported in Tables 1 and 2.

Material and Methods:

Czapek Malt Agar (Himedia laboratories Ltd.) was used for culturing *Tricholphytos mentagrophytes T. tonsurans, T. violaceum, Aspergillus fresnil* and *A niger, A. japonicus*. Mucological Agar (Himedia Laboratories Ltd was used for *Cryptocaccus neoformans* and *Candida* sp.

Reference Compounds:

Amphotercin B and Nystatin (Himedia Laboratories Ltd.) were used as standards for comparison.

Fungal Strains:

Pathogeiic fungal strains of yeast and filamentous fungi (Identified and gifted by Dr. Savio from Goa Medical College, Bamoblim) were used for the test. Strains of *Aspergillus* were isolated from the infected wheat bread with sterile needles; fungal material was surface sterilized using 0.5% sodium hypochlorite for 2-3 minutes and then washed with small brush in sterile distilled water. This *Aspergillus* species was described earlier as food spoilage (Bhosale et. Al., 1999). Washed fungal material was transferred using needle into the sterile culture media and subcultured for purification by following standard methods (Collins and Taylor, 1967). Taxonomic identification was done by using various standard keys (Ainswort et at., 1973; Onion et al., 1981 (and identification confirmed by Dr. (Mrs.) Alka Pandey of Agarkar Research Institute, Pune)

Preservation of Fungal Strains:

Yeast strains (*Candida* sp and *Cryptococcus neoformans*) were maintained by single colony transfer on mycological agar (Himedia Laboratories Ltd.) at the refrigeration temperature (3-5° C.). Filamentous fungi were maintained on Czapek Malt Agar slants at refrigeration temperature (3-5° C.), until needed for the assay.

Assay Protocols:

Disk Dissuasion Assay:

The disk diffusion assay was used for screening of antifungal activity of the compound. The stock solution for the test was prepared by dissolving 5 mg of Cyclosporin A in in 200 µl dimethylsuifoxide (DMSO). From the stock solution 10 µl were spread on the paper disc so as to obtain the final concentration of 250 µg disk$^{-1}$. Control disk was applied reconstituted with only dimethylsulphoxide and were dried at 28-29° C. Completely dried disk was applied to inoculated plates. The plates were incubated at room temperature for the period between 42-120 hrs. to obtain maximum growth in the culture media. The zones of inhibition around the disks were measured. The results obtained in these bioassays are summarized in Table 1.

TABLE 1

Antifungal activity of cyclosporin A from *Fusarium nivale*. (250 µg. disk$^{-1}$)

| Microorganisms used | Disk diffusion method Inhibition zone |
|---|---|
| *Aspergillus fresenii* | 5 mm |
| *A. juponicus* | 5 mm |
| *A. niger* | 3 mm |
| *Cryptococcus neoformans* | 5 mm |
| *Candida sp.* | 5 mm |
| *Trichophyton mentagrophytes* | 5 mm |
| *T. tonsurans* | 6 mm |
| *T. violaceum* | 5 mm |
| *Fusarium* sp. | 4 mm |

Minimum Inhibitory Concentration (MIC):

Innocula were adjusted to 50 μl of *Cryptococcus neoformans, Candida* sp., *Trichophyrou tonsurans, T. violaceum* and *T. mentagrophytes, Aspergillus fresenil, A. niger, A. japonicus* and spread on the appropriate plates, excess moisture was allowed to be absorbed for 10 minutes before applying on disks. Immediately prior to the assay, the testing compound of cyclosporin, object of the present invention, the reference compounds amphoteroin B and nystatin, potency approx. 750 μg/mg and 4800 USP unit/mg respectively, were reconstituted in triplicate in dimethylsulfoxide. The stock solution for the MIC was prepared by dissolving 1 mg and 0.25 mg in 200 μl of dimethylsulfoxide (DMSO) and 0.625 mg, 0.312 mg in 1 ml of dimethylsulfoxide (DMSO). From the stock solution 10 μl were spread on the paper disk so as to obtain final concentration of 50, 25, 12.5, 6.25 and 3.12 μg $disc^{-1}$. Disks were dried at reduced pressure in a dessicator, at 28-29° C. and applied to inoculated plates. Test plates were incubated for 42-120 hrs. at room temperature to obtain maximum growth and MIC was determined as lowest concentration of compound and antifungal agents resulting in a cleas zone of growth inhibition.

In testing, the cyclosporin A was constituted in dimethylsulfoxide (DMSO) immediately prior to all assays. Dimethylsulfoxide (DMSO) alone had no detectable inhibitory effect on any of the tested microbes. Cyclosporin A was tested against a diverse collection of yeast and filamentous fungi, some of which, are resistant to the reference compound nystatin. Filamentous fungi were nystatin resistant.

The in vitro antifungal activity of cyclosporin A, object of the present invention in disk, diffusion method is summarized in Table 2.

TABLE 2

MIC (μg/$disc^{-1}$) for antifungal activity of compound of cyclosporin A

| Microorganism Used | Disk Diffusion Method: Cyclosporin A μg/$disc^{-1}$ | Amphotericin B μg/$disc^{-1}$ | Nystatin μg/$disc^{-1}$ |
|---|---|---|---|
| *Aspergillus Fresenii* | 25-50 | 6.25-12.5 | — |
| *A. Japonicus* | 12.5-25 | 6.25-12.5 | — |
| *A. Niger* | 25-50 | 6.25-12.5 | — |
| *Cryoticiecus Neoformans* | 12.5-25 | 3.12-6.25 | 3.12-6.25 |
| *Candida* sp. | 12.5-25 | 3.12-6.25 | 3.12-6.25 |
| *Trichophyton Mentagrophytes* | 25-50 | 3.12-6.25 | — |
| *T. tonsurans* | 12.5-25 | 6.25-12.5 | — |
| *T. violaceum* | 25-50 | 6.25-12.5 | — |
| *Fusarium* sp. | 25-50 | 12.5-25 | — |

The present invention is regarding the isolation of cyclosporin A from a new fungal source, viz, *F. nivale,* associated with *Portersia coarctata* and evaluation of its antifungal properties. This study relates to an in vitro novel use of cyclosporin A against the food spoilage *Aspergillus* strains (*A. fresenii, A. japonicus* and *A. niger*).

The fungus used in the present invention, *Fusarium nivale*, was deposited under the Budapest Treaty with the Microbial Type Culture collection & Gene Bank (MTCC), Institute of Microbial Technology, located at Sector 39-A, Chandigarh 160036, INDIA, under Deposition No.: MTCC 5221.

It further explains antifungal activity and MIC of commonly occurring dermatophytic strains (*Cryptococcus neoformas, candida* sp. *Trichophytan mentagrophytes, T. rubrum, T. violaceium, T. tonsurans* and *Fusarium sp.*).

REFERENCES CITED

U.S. Pat. No. 5,409,806 April 1995 Lundell et. al. 435/713

OTHER REFERENCES

1. Ainswort G. C. et al., Eds. The fungi: An advanced treatise. New York/London: Academic Press. 1973. A taxonomic review with keys: Ascomycetes and fungi imperfecti, Vol. IV A.
2. Bhosale et Al., 1999. Antifungal activity of some marine organisms from India, against food spoilage *Aspergillus* strains. Mycopathologia. 147: 133-1389.
3. Booth, C., 1971. The genus *Fusarium*. Common. Mycol. Inst., Kew. 237 pp.
4. Borel, J. F. 1986 Cyclosporin A and its future. Progr. Allergy 38:9-18.
5. Chen C., Imamura, N., Nishijima, M., Adachi, K. Sakai, M. Sano, H. 1996. Halymecins, new antimicroalgal substances produced by fungi isolated from marine algae. 44:10 998-1005.
6. Collins C. H. et. Al., sec. Eds. Microbiological methods. New York. Plenum Press, 1967.
7. Dreyfus, M. et. Al., 1976. Cyclosporin A and C a new metabolites from *Trichoderma polysporium* (link express) Rifia Eur. J. Appl. Microbiol. 45: 1223-1228.
8. Mall O. P. and S. K. Chauhan, 1990. *Fusarium mycotoxins:* An overview, In Hasija, J. K. and K. S. Bilgrami, Internation Bioscience Series Volume 15. Perspective in mycological Research Vol.-II. Today and Tomorrow's Printer and Publishers. 247-260.
9. Onion A. H. S. et. Al., 1981. Sec. Eds. Smith's introduction to industrial mycology. London Edward Arnold Publishers.
10. Rahacek Z. and DeXiu Z., 1991. The biochemistry of Cyclosporin formation-A review. Process Biochem., 26: 157-166.
11. Ramana Murthy et. Al., 1999 Cyclsporin Production by *Tolypooladium inflatum* using solid state fermentation, 34: 269-289.
12. Ruegger et. al., 1976. Helv. Chim. Acta, 59: 1075.
13. Saawi, K. et. Al., 1981 Isolation and properties of two antifungal substances from *Fusarium solani,* Agric. Biol. Chem. 45(5) 1223-1228.
14. Stiller C. R. aud Opelz G., 1991. Should Cyclosporin be continued indefinitely? Transplant Proc., 23: 36-40.
15. Ueno Et. Al., 1977. Toxicological approaches to the metabolites of Fusaria-II Trichothecenes and Zearalenone one from *Fusarium* species isolated from river sediments. 3: 177-184.
16. Weiser J. and Matha V., 1988. The insecticidal activity of cyclosporin A on mosquito larvae. J. Inver. Pathol. 51: 92-93.

The invention claimed is:

1. A process for the isolation of the pharmaceutically active compound cyclosporin A from the fungus *Fusarium nivale*, comprising the steps of:

a) washing the leaves of *Porteresia coarctata* with sterile sea water, b) allowing the fungus to grow and sporulate onto the leaves in moisture condition, c) identifying the fungus grown onto the leaves as *Fusarium nivale*, d) purifying a colony of fungus *Fusarium nivale* of step (c), e) transferring the purifed colony of step (d) by a nichrome loop into sterile culture media, f) growing the culture media of step (e) containing nutrient both with sea water and standard medium of three weeks under stationary condition, g) removing biomass of the fungi of step (d) after a predetermined growth is achieved, h) freeze drying the biomass of step (g), i) extracting the freeze dried biomass of step (h) with a ketonic solvent, j) concentrating the ketonic solvent of step (i) under reduced pressure and a temperature of about 30° C. to obtain an extract, k) adding water to the extract of step (j), l) extracting the aqueous extract of step (k) with petroleum ether, followed by ethyl acetate, separating the organic layers and aqueous solution, m) evaporating the ethyl acetate extract of step (l) to obtain concentrated ethyl acetate extract, and n) purifying concentrated ethyl acetate extract of step (in) by repeated gel chromatography using Sephadex LH-20, eluting with cholorform-methanol (1:1) to obtain pure cyclosporin A.

2. The process as claimed in claim 1, wherein in step (c) the sterile culture media comprises malt agar.

3. The process as claimed in claim 1, wherein in step (g) the ketonic solvent used is selected from the group consisting of acetone, ethyl methyl ketone, and methyl isobutyl ketone.

* * * * *